(12) United States Patent
Krutzik et al.

(10) Patent No.: US 8,999,652 B2
(45) Date of Patent: Apr. 7, 2015

(54) BIOLOGICAL ENCODING OF LARGE NUMBERS OF CELLS

(75) Inventors: Peter Oliver Krutzik, Los Altos, CA (US); Thomas Scott Wehrman, Sunnyvale, CA (US)

(73) Assignee: Primity Bio, Inc., Santa Clara, CA (US)

( * ) Notice: Subject to any disclaimer, the term of this patent is extended or adjusted under 35 U.S.C. 154(b) by 580 days.

(21) Appl. No.: 12/733,056

(22) PCT Filed: Aug. 5, 2008

(86) PCT No.: PCT/US2008/009396
§ 371 (c)(1),
(2), (4) Date: Apr. 13, 2010

(87) PCT Pub. No.: WO2009/023107
PCT Pub. Date: Feb. 19, 2009

(65) Prior Publication Data
US 2010/0203543 A1    Aug. 12, 2010

Related U.S. Application Data

(60) Provisional application No. 60/955,038, filed on Aug. 10, 2007.

(51) Int. Cl.
| | |
|---|---|
| *G01N 33/567* | (2006.01) |
| *C12P 21/06* | (2006.01) |
| *G01N 33/532* | (2006.01) |
| *G01N 33/533* | (2006.01) |
| *G01N 33/569* | (2006.01) |

(52) U.S. Cl.
CPC ............................. *G01N 33/56966* (2013.01)

(58) Field of Classification Search
USPC .............. 435/7.2, 40.5, 455, 347, 362, 287.2, 435/7.21, 69.1; 436/35, 56, 63, 164, 171, 436/172, 173, 544, 546; 422/82.05, 82.09
See application file for complete search history.

(56) References Cited

U.S. PATENT DOCUMENTS

| | | | |
|---|---|---|---|
| 8,003,312 B2* | 8/2011 | Krutzik et al. .................... | 435/4 |
| 2005/0009060 A1* | 1/2005 | Beernink et al. .................. | 435/6 |
| 2005/0037437 A1 | 2/2005 | Zeidler | |
| 2008/0138820 A1* | 6/2008 | Thomas ........................... | 435/6 |
| 2008/0241820 A1 | 10/2008 | Krutzik | |

FOREIGN PATENT DOCUMENTS

WO        2009023107 A1    2/2009

OTHER PUBLICATIONS

Kotecha, "Cytobank—web-based phospho-flow cytometry analysis and collaboration," Power point presentation, Mar. 22, 2007.
Holbeck, "Update on NCI in vitro drug screen utilities," European Journal of Cancer 40:785-793 (2004).

(Continued)

*Primary Examiner* — Gail R Gabel
(74) *Attorney, Agent, or Firm* — Cooley LLP (57) ABSTRACT

Mixtures of cell types can be analyzed by having at least two signal markers, with at least one at three different levels to provide a barcode for each cell type. The mixture of cells may be subjected to a common candidate moiety and the effect of the moiety on the cells determined along with identification of the cell by the barcode. Conveniently, surface marker proteins and labeled antibodies can be used to create the barcode and the cells analyzed with flow cytometry.

24 Claims, 6 Drawing Sheets

(56) References Cited

OTHER PUBLICATIONS

Krutzik and Nolan, "Intracellular Phospho-protein staining techniques for flow cytometry: monitoring single cell signaling events," Cytometry Part A 55A:61-70 (2003).

Krutzik and Nolan, "Fluorescent cell barcoding in flow cytometry allows high-throughput drug screening and signaling profiling," Nature Methods 3(5):361-368 (2006).

Krutzik et al., "High-content single-cell drug screening with phosphospecific flow cytometry," Nature Chemical Biology 4(2):132-142 (2008).

Russello, "Assessing cellular protein phosphorylation: high throughput drug discovery technologies," Assay and Drug Development Technologies 2(2):225-235 (2004).

Saunders et al., "High-throughput multiplex flow cytometry screening for botulinum neurotoxin type A light chain protease inhibitors," Assay and Drug Development Technologies 8(1):37-46 (2010).

Schulz et al., "Single-cell phospho-protein analysis by flow cytometry," Current Protocols in Immunology, Supplement 78, 8.17.1-8.17.20 (2007).
Simons et al., "Duplexed, bead-based competitive assay for inhibitors of protein kinases," Cytometry Part A 71A:451-459 (2007).
Sklar et al., "Flow cytometry for drug discovery, receptor pharmacology and high throughput screening," Curr Opin Pharmacol 7(5):527-534 (2007).
Young et al., "Duplex high throughput flow cytometry screen identifies two novel formylpeptide receptor family probes," Cytometry A 75(3):253-263 (2009).
Chapman, T., Drug discovery: The leading edge, Nature, 430:109-115, 2004.
Feng, X.D. et al, Analysis of Pathway Activity in Primary Tumors and NCI60 Cell Lines Using Gene Expression Profiling Data, Genomics Proteomics Bioinformatics, 5:15-24, 2007.
Harris, R.A. et al., Cluster analysis of an extensive human breast cancer cell line protein expression map database, Proteomics, 2:212-223, 2002.
Hood, L. et al., The impact of systems approaches on biological problems in drug discovery, Nat Biotechnol, 22: 1215-1217, 2004.
Krutzik, P.O. et al., Analysis of protein phosphorylation and cellular signaling events by flow cytometry: techniques and clinical applications, Clin Immunol, 110: 206-221, 2004.
Krutzik, P.O. et al., Coordinate analysis of murine immune cell surface markers and intracellular phosphoproteins by flow cytometry, J Immunol, 175:2357-2365, 2005.
Krutzik, P.O. et al., Characterization of the murine immunological signaling network with phosphospecific flow cytometry, J Immunol, 175:2366-2373, 2005.
Paull, K.D. et al., Display and analysis of patterns of differential activity of drugs against human tumor cell lines: development of mean graph and Compare algorithm, J Natl Cancer Inst, 81(14):1088-1092, 1989.
Shoemaker, R.H., The NCI60 human tumour cell line anticancer drug screen, Nat Rev Cancer, 6:813-823, 2006.
Suggitt, M. et al., 50 years of preclinical anticancer drug screening: empirical to target-driven approaches, Clin Cancer Res, 11:971-981, 2005.
Tan, T.W. et al., Curcumin-induced cell cycle arrest and apoptosis in human acute promyelocytic leukemia HL-60 cells via MMP changes and caspase-3 activation, Anticancer Res, 26:4361-4371, 2006.
Tarnok, A. et al., Cytomics—importance of multimodal analysis of cell function and proliferation in oncology, Cell Prolif, 39:495-505, 2006.
Williams, K. et al., Analysis of differential protein expression in normal and neoplastic human breast epithelial cell lines, Electrophoresis, 19:333-343, 1998.
Zhu, Y. et al., Estrogen receptor alpha positive breast tumors and breast cancer cell lines share similarities in their transcriptome data structures, Int J Oncol, 29:1581-1589, 2006.
PCT/US2008/009396, ISR mailed Nov. 4, 2008. (2 pages).
PCT/US2008/009396, Written Opinion mailed Nov. 4, 2008. (4 pages).
PCT/US2008/009396, IPRP dated Sep. 16, 2009. (7 pages).
EP08795032, EP Search Opinion and Supplementary EP Search Report dated Jul. 7, 2010. (3 pages).

* cited by examiner

BIOLOGICAL ENCODING OF LARGE NUMBERS OF CELLS

CROSS-REFERENCE TO RELATED APPLICATIONS

This application is a §371 filing of PCT/US2008/009396, filed Aug. 5, 2008, and claims the benefit under 35 U.S.C. §119(e)(1) of U.S. Provisional Application No. 60/955,038, filed Aug. 10, 2007, which applications are incorporated herein by reference in their entireties and from which applications priority is claimed pursuant to the provisions of 35 U.S.C. §§119/120.

TECHNICAL FIELD

The present invention relates to biological encoding of cells, particularly when associated with monitoring cellular events.

BACKGROUND

High throughput screening (HTS) of chemical libraries has become an invaluable tool in the search for drugs [1] and in screening for ancillary activities other than related to a target. Technological advances in synthetic chemistry, robotics, and assay design have greatly increased the efficiency of these screens, leading to a dramatic increase in the number of biologically active small molecule candidates. However, with thousands of potential drug candidates it is becoming increasingly difficult to decide on which candidates to move forward. Current methodologies that analyze a single cell type and single parameter often do not provide sufficient information to make decisions on which compounds are ideally suited to a particular indication. Since the vast majority of resources in preclinical drug discovery are spent on compounds that ultimately fail, it is critical to eliminate as many of these poor leads as early in the drug discovery process as possible. By gathering more compound-specific data earlier, non-specific and toxic lead compounds can be discarded sooner, accelerating drug discovery while minimizing the use of precious resources. Thus the current challenge is generating higher-throughput, more informative, secondary screening assays [2, 3].

Secondary screening assays for cancer or other therapeutics should minimally be able to report on the biological activity, cellular toxicity, membrane permeability, and selectivity of the compound for cancer or other diseased cells relative to normal tissue [4]. The advent of cellular high content screening provides a method of obtaining this information simultaneously [5]. Indicators of cellular toxicity, biological activity and mechanism of action can be examined concurrently in a cellular context providing multiple data points from a single sample. Importantly, high content screening by flow cytometry or microscopy techniques allows these multiple parameters to be measured for each individual cell in the sample [6-12]. Assaying multiple events at the single cell level, particularly with involvement of numerous cells having the same phenotype, produces more robust correlations between signaling events and cellular responses, and enables the researcher to decipher coincident and interrelated effects. These attributes make high content, single-cell assays more than the sum of their parts.

With the ever increasing importance of cancer with an aging population, the development of secondary, high content assays for cancer therapeutics is particularly challenging due to the inherent diversity of this disease. Thousands of different combinations of cellular alterations can lead to oncogenic transformation and disparate cellular phenotypes making it impossible to choose one cell line as a model. As an example, a profile of the 11 breast cancer cell lines derived from patient samples in the MD Anderson Cancer cell line database was analyzed using six parameters from each (Table I). Although similarities exist, this relatively small subset of parameters reveals that no two cell lines are identical. The disparities range from physical attributes such as metastatic potential and invasion, to gene expression and mutation.

Although the validity of using cell lines as model systems is debated, in screening assays they are often a necessity [4] and researchers have found striking similarities between commonly used breast cancer cell lines and fresh tumor explants [13]. Since a representative breast cancer cell line does not exist, candidate compounds are typically tested across panels of cell lines [14]. However no consensus panel is routinely used: the NCI chose nine cell lines to profile against known cytotoxic agents, MD Anderson selected an overlapping yet distinct set (which can be found on the World Wide Web at mdanderson.org), and 'omics studies by the Ludwig Cancer Institute [15] and the Argonne national laboratories [16] chose still another set of cell lines as representative. Importantly the responses of these cell lines varied up to 100-fold in their sensitivity to specific drugs emphasizing the importance of profiling chemotherapeutic agents across a wide array of sample cell lines [14].

TABLE I

| Cell Line | invasion in vitro | ER expression | Caspase | metastasis | PAI-1 | p53 |
|---|---|---|---|---|---|---|
| BT-20 | + | + | n/a | neg | + | n/a |
| BT-474 | + | + | n/a | + | − | m |
| Hs578T | + | − | + | + | + | m |
| MCF-7 | + | + | − | +/− | +/− | wt |
| MDA-MB-231 | + | − | + | − | + | m |
| MDA-MB-361 | − | + | n/a | − | − | n/a |
| MDA-MB-435 | + | − | − | + | + | m |
| MDA-MB-468 | + | − | n/a | − | n/a | m |
| SK-BR-3 | +/− | − | n/a | n/a | + | m |
| T-47D | +/− | + | + | n/a | − | m |
| ZR-751 | +/− | + | n/a | n/a | − | wt |

In order to ensure the relevance of secondary screening assays and improve their predictive power, it is necessary to multiplex quantitative, high-content experimental analysis across an array of cell types. Compounds that are generically toxic to non-cancerous cells could be defined by including non-breast cancer cell lines or primary cell samples in the analysis. Drugs highly selective for these other cell lines can be eliminated from the discovery process or assigned to other development programs focused on those particular cellular models. In addition, the profile of responding cell lines is highly informative since many of these cell lines have been genetically and phenotypically characterized [17, 18]. Common features of cell lines that respond or are resistant to treatment with a particular compound can be used to infer mechanism of action of the compound and identify patient populations who may benefit from treatment more than others [19]. Although these types of datasets can be obtained using traditional methods, the amount of test compound, the cost of high content assays, and the manpower necessary to profile the cellular responses of dozens of cell lines against hundreds of samples is prohibitive. Therefore, this type of exhaustive secondary screening is typically only performed on a few lead compounds with large supplies of material available and with a high degree of confidence in its success.

There is, therefore, a crucial need for methods that drastically reduce the cost of screening, permit relatively low amounts of sample candidates to be used, are a rich source of information as to the biological properties of the sample candidate and provide a robust response with a high degree of confidence in the results.

SUMMARY OF THE INVENTION

An assay platform is provided employing multiple signals distinguishing individual cell clones in a varied mixture of cell clones. Each cell is labeled with a minimum of two signal markers, with at least one at three levels of the signal marker, and with at least one genetically encoded, such that 6 or more different cell types can be identified per sample. Each cell is barcoded by the amount and type of the signal markers. By providing for a distinctive signal produced in response to a stimulus, e.g. sample candidate, the cells can be screened for a response to the stimulus and the particular cell identified.

Thus, in one embodiment, the invention is directed to a method of distinguishing between cell types in a sample comprising a population of cells which comprises a plurality of different cell types. The cell types are distinguishable by at least two different signal markers at least one of which is distinguishable at three different levels. At least one signal marker is expressed from a genetic construct, such that the combination of amount and type of signal markers provide a unique barcode for a specified cell type. The method comprises detecting from at least one of the cell types the at least two different signal markers, whereby one of the plurality of cell types is distinguished.

In certain embodiments, the signal markers are detected by fluorescence and the three different levels are absence of fluorescence, and fluorescence at two different intensities. In other embodiments, the least two different cell types fluoresce at different wavelengths.

In additional embodiments, the population of cells comprises an identifiable response marker distinguishable from the signal markers and produced in relation to activity of a cellular pathway.

In yet further embodiments, at least one of the signal markers is a cell surface marker and prior to detecting, the method comprises combining the cells with antibodies to the cell surface marker. The antibodies are conjugated to at least one of different fluorescers or different numbers of fluorescers, or to mass isotope labels.

In certain embodiments the signal markers are detected by fluorescence and said detecting is by means of flow cytometry.

In further embodiments, at least one of said signal markers is an intracellular protein.

In yet additional embodiments, the signal markers are detected using mass labels and detecting is by means of mass spectrometry.

In certain embodiments, the plurality of cell types is at least 6 different types.

In another embodiment, the invention is directed to a method of distinguishing between cell types in a sample comprising at least 6 different cell types, wherein the cell types are distinguishable by at least two different signal markers at least one of which is expressed from a genetic construct and at least one of which is distinguishable at three different levels, such that the combination of amount and type of identifiable marker provide a unique barcode for a specified cell population. The method comprises detecting from at least one of the cell types at least two different signal markers by flow cytometry, whereby one of the cell types is distinguished.

In certain embodiments, the detecting includes detecting a fluorescent signal from an intracellular protein.

In additional embodiments, the method comprises the additional step of fixing and permeabilizing the plurality of different cell types.

In yet further embodiments, the cells produce at least two surface markers, at least one of which is exogenous to the cells and the three levels are a result of different levels of expression of the surface markers, and prior to detecting, the cells are combined with antibodies to the cell surface marker, wherein the antibodies are conjugated to at least one of different fluorescers or different numbers of fluorescers.

In additional embodiments, the invention is directed to a method of screening a candidate moiety for its effect on cell types, employing a sample containing a plurality of different cell types distinguishable by at least two different signal markers at least one of which is distinguishable at three different levels and at least one of which is expressed from a genetic construct, such that the combination of amount and type of identifiable marker provide a unique barcode for a specified cell population. The method comprises combining the sample with a candidate moiety for sufficient time for any effect resulting from the candidate moiety to occur; detecting from at least one of the cell types at least two different signal markers and the result of the effect; whereby said result is related to said one of said cell types.

In other embodiments, the invention is directed to a mixture of cells comprising at least 6 different cell types, each cell type comprising at least two genetic constructs which express proteins exogenous to the cell types, wherein the expression of at least one of the proteins is detectable at least at three different levels, wherein the cell types can be distinguished by binding labeled antibodies to the proteins of each cell, each protein binding to a different labeled antibody, and/or by expression of a fluorescent protein by the genetic construct. In certain embodiments, the labeled antibodies are bound to the proteins.

In an additional embodiment, the invention is directed to a kit comprising a mixture of cells as detailed above; and the labeled antibodies.

These and other embodiments of the subject invention will readily occur to those of skill in the art in view of the disclosure herein.

BRIEF DESCRIPTION OF THE FIGURES

FIG. 4. Barcoding of six cell populations using two genetically introduced signal markers, CD8 and CD19. Human MDA-MB-231 breast cancer cells were transduced with vectors containing murine CD8 and murine CD19 surface proteins. The cells were stained with fluorescently labeled antibodies against CD8 (APC) and CD19 (PE). Clones that displayed differential expression levels of CD8 and CD19 were sorted by FACS and grown for analysis. (a) Histogram analysis of six isolated and passaged clones. Clone 19a2 is negative for both CD8 and CD19 expression. Clones 19a5, 19b4, and 19d4 express different levels of the marker CD19, but do not express CD8. Clones 8c1 and 8c4 express different levels of the marker CD8, but do not express CD19. (b) Two dimensional dot plot analysis showing discrimination of all six clones based on their expression levels of the two signal markers CD8 and CD19. Each population can be resolved with greater than 90% purity for over 60% of the cells within the population. Note that these populations represent expansion of a single clone through approximately 15 cell doubling periods.

FIG. 5. Barcoding of six Hek293 cell populations using one genetically introduced signal marker, CD19, and one exogenously added fluorescent dye, Pacific Blue. In this experiment, three Hek293 clones expressing none, medium, or high levels of CD19 were either left unlabeled, or were labeled with 5 ug/ml of Pacific Blue NHS directly in medium (MEM+5% FBS) after trypsinization to remove them from the culture plastic. After 15 min, the cells were washed and then both the labeled and unlabeled cells were stained with anti-CD19 PE. (a) Histogram analysis showing the three populations labeled with Pacific Blue distinguishable from the unlabeled cells. Note that the CD19 staining levels do not change with the addition of the small molecule dye. (b) Two dimensional dot plot showing the six cell populations. All six populations can be identified with greater than 90% purity for over 60% of the population.

FIG. 6. Barcoding of five cell populations (two Hela and three Hek293) using one genetically introduced signal marker, CD19, and one inherent genetic signal marker, EGFR. Shown is a two-dimensional plot distinguishing the five cell populations. Three clonally sorted Hek293 clones are separated based on their expression of CD19. Two clonally sorted Hela clones are also separated based on their expression of CD19. In addition, Hela cells express endogenously high levels of epidermal growth factor receptor (EGFR) which distinguishes them from the Hek293 cells, which express low to moderate levels of the receptor. In this case, the anti-CD19 antibody was conjugated to PerCPCy5.5 and the anti-EGFR antibody to PE. Note that cells were cloned based on expression of the introduced CD19 signal marker. No special steps were taken to sort based on EGFR expression, which is endogenous to the particular cell types.

DESCRIPTION OF THE SPECIFIC EMBODIMENTS

In accordance with the subject invention methods and compositions are provided for multiplexing cellular events using a mixture of different cell types for response to one or more stimuli. Each of the cell types, particularly mammalian, is encoded using at least two signal markers or indicators, wherein at least one indicator is present at least at three different levels. Each cell type has at least two cellular markers, one of which is exogenous to the host cell that provide for a combination of different signals. A mixture of cells having different phenotypes is subjected to one or more stimuli, e.g. candidate biologically active compounds that may result in a change in the state of the cell. The change in the state of the cell will result in a detectable observation. The mixture may then be analyzed using a separation method, such as flow cytometry or mass spectrometry, where the state of the cell and its identity are determined.

By level is intended that each cell type be readily distinguished from other cell types by the method of analysis, so that there is little, if any, interference in detecting a specific cell type. For example, at least 50% of the cells of each cell type in a mixture can be measured with a purity of greater than 80% using the combination of signal markers. As an illustration, in flow cytometry one could use the middle 50% of cells of a given cell type as measured by their fluorescence intensity at each channel, where at least 80% of such cells would be of the same cell type.

The signal markers or indicators can be varied to provide for different types and amounts, where the amounts are measurable using applicable instrumentation. Signals that can be individually detected include fluorescent signals, size, isotopic, luminescent, light absorption, atomic or molecular weight, and the like.

Depending upon the nature of the assay, different cell types will be employed, that is a cell type has a phenotype that is distinguishable for the purposes of the assay from another cell type. For example, the cells may have different phenotypes. For the most part, cell lines will be employed, frequently transformed cell lines, that provide the surface markers for distinguishing the cells. For mammalian cells, the cells may be derived from any organ, including blood, heart, brain, kidney, pancreas, liver, lung, gut, lymph node, etc, and may be epithelial, endothelial, myocardial, leukocyte, lymphocyte, neuron, glial, etc.

Each of the cells will be transformed to include at least one protein marker, frequently two protein markers and may have as many as four or more markers. A protein marker can be introduced into the cells using a variety of vectors or bare DNA comprising a genetic construct capable of expressing the protein marker in the host cell. Each of the cells will have at least two protein markers, including endogenous and exogenous markers, there being at least one exogenous marker. The exogenous markers may come from different cell types from the host cell, e.g. lymphocyte for hepatic cells, may come from different species, e.g. murine for primate host cells, synthetic peptides, saccharides, lipids, etc. The different levels may be achieved in a variety of ways. One way is the expression level of a single marker, using different promoters, with or without enhancers, random integration and selecting cells with different levels of expression, providing for integration at specific sites having different levels of expression at the sites, e.g. Cre-lox. Another way is to use different epitopes, such as different marker proteins, that are detected at different levels within the same parameter, e.g. using antibodies of different binding affinities. Another method is to use multiples of the same epitope on a single molecular scaffold with relatively similar expression levels of the scaffold in or on different cells.

While for the most part, the signal marker will be the expression product of a gene, either exogenous or endogenous, in some instances the signal marker may be the result of processing of the expression product, such as cleavage, glycosylation, etc., where the product of the processing will serve as the signal marker.

Depending upon the method of detection of the markers, various reagents will be employed. In one aspect, labeled binding proteins, such as antibodies can be employed, where the label can be detected, such as fluorescers, isotopes, metal atoms or ions, chemiluminescers, etc. Other binding proteins include enzymes, lectins, or other naturally occurring binding proteins. With antibodies one may use a single labeled antibody or use an unlabeled antibody binding to the marker and a second labeled antibody binding to the unlabeled antibody. In another aspect, differential expression can be employed, such as expressing a binding protein, e.g. strept/avidin, which can be coupled with labeled biotin, or expressing a fluorescent protein, such as GFP, YFP, RFP, etc.

Fluorescent labels of interest include but are not limited to small molecule dyes such as Pacific Blue, Pacific Orange, Alexa 488, Alexa 555, Alexa 594, Alexa 610, Alexa 647, Alexa 700, Alexa 750, Alexa 790, Cy3, Cy5, Cy5.5, Cy7, DyLight 488, Dylight 633, Dylight 649, Dylight 750, Dylight 800, IRDye 800, FITC, TRITC, Texas Red; protein fluorophores such as phycoerythrin (PE) and its tandem conjugates such as PE-Cy5, PE-Cy5.5, and PE-Cy7, allophycocyanin (APC) and its tandem conjugates APC-Cy5.5 and APC-Cy7; and nanoparticles such as Quantum Dot 525, 565, 605, 655, 705, and 805.

Frequently, one will be interested in the effect of a candidate moiety on a cellular pathway. While the candidate moiety will usually be a compound, naturally occurring or synthetic, it also includes mixtures of compounds, such as blood, plant extracts, lysates, interstitial fluids, cells, etc. The effect may be determined in a variety of ways, depending upon the particular event that occurs, e.g. degradation, phosphorylation, acylation, acetylation, sumoylation, ubiquitination, complex formation, initiation or inhibition of transcription or expression, enzyme activation or inhibition, receptor dimerization, receptor complexing, receptor binding, receptor activation, etc. In most cases there will be a response signal produced, either directly or indirectly, that will be detected to determine the effect on the cellular pathway.

In carrying out the assay, a library of cells would be formed. The library may have cells sharing at least one common characteristic associated with the assay. Characteristics of interest include but are not limited to origin, cell type, cell line, growth properties, tissue type, response to stimulus, receptor expression, genetic alterations, etc. The library will be at least $10^2$ cells, more usually at least about $10^3$, and frequently may be $10^4$ or more, generally less than about $10^9$, more usually less than about $10^8$. There will be at least about 6 different cell types, frequently at least about 9 cell types, usually at least about 12 cell types, and usually not more than about $10^3$, generally not more than about $5 \times 10^2$.

It is to be understood that in referring to the size of the library, one could start with a library as described above and then transform with a genetic library, e.g. a DNA library, a viral library, etc., whereby the cell types would be greatly expanded, including up to about $10^7$ cell types.

Conveniently, the libraries can be prepared and stored for future use. The libraries may be frozen and thawed prior to use or maintained in an appropriate medium. Thus, a mixture of cells comprising at least 6 different cell types, each cell type comprising at least one expression construct expressing a signal marker. The signal markers may be surface membrane or intracellular proteins, usually at least one being a surface marker. Different cell types having different levels of expression of said signal markers provide for differentiation. Conveniently, the cell types can be distinguished by binding labeled antibodies to the signal markers of each cell, where each of the labeled antibodies bound to a cell are differently labeled. For example, one could use different antibodies labeled with different fluorescers. Alternatively, one could have the same level of expression of the signal marker proteins, but have the signal marker proteins of each cell type individually bound to antibodies having different levels of substitution of the label. One can bind the antibodies before or after adding the candidate moiety. In the latter instance, the cells would be subjected to a candidate moiety with the antibodies present on the surface. At the end of an assay in both situations, one will have a mixture of cell types, where each cell type has an identifying barcode. There may also be at least one other signal associated with a cell type resulting from the activity of the candidate moiety.

The cells for the assay may be pretreated by starvation, synchronization, stimulation, inhibition, transduced or transfected, irradiation, etc.

After pretreatment, if any, the cells in an appropriate medium are then ready for use in the assay. In one application the cells are placed in an assay container, conveniently a microtiter well plate and exposed to a candidate moiety. Alternatively, flow systems may be used to create distinct samples, compound gradients, temporal separation, etc. By injecting a candidate moiety in one stream where the moiety undergoes dilution and then mixing with the cell stream, one can provide for exposing the cells stream to a moiety gradient. Alternatively one may inject different moieties at different times into the cell flow stream to provide for cell aliquots that are exposed to different moieties. For temporal separation, one samples the cell flow stream at different sites along the flow stream where the cell at the site have been exposed for a predetermined time to the moiety at each of the sites.

The results of the assay or action resulting from the presence of the candidate moiety will be detected in accordance with the nature of the barcode and the method for detecting any changes in the cell as a result of interacting with the candidate moiety. When determining cell count, size or granularity, the cells would be analyzed in a flow cytometer. For determining cell cycle, one would combine the cells with a DNA fluorescent dye and determined in a flow cytometer. One may use vital dyes for cell health, e.g. mitochondrial potential, membrane potential, apoptosis, etc. Where reporter genes are employed, when functional enzymes are produced, enzymatic substrates producing a detectable product, e,g. fluorescer, are employed.

For detecting an intracellular protein, the cells may be fixed and permeabilized to introduce a labeled antibody, a small molecule that binds to an intracellular protein, etc.

As illustrative of the subject methodology, one creates 27 uniquely barcoded breast cancer cell lines. Each of the cell types will provide for a different detectable signature or barcode, using three signal markers at three levels each. Five cellular parameters relevant to the secondary screening of cancer therapeutics are chosen to be used in conjunction with a breast cancer panel: cell cycle, cell growth, p38 phosphorylation as a marker of cellular stress, p53 phosphorylation as a marker of DNA damage, and Caspase-3 cleavage as a marker of apoptosis. Once the cell lines are barcoded, using conventional methodologies the effects of eight widely utilized chemotherapeutic agents are analyzed across the panel. The cells are fixed and permeabilized in accordance with conventional procedures, labeled antibodies against the intracellular proteins of interest are added and then the cells are analyzed on a flow cytometer. This panel allows the measuring of the $IC_{50}$, $GI_{50}$, and $LC_{50}$ profiles of each of these molecules.

In a second illustration, cells of a cell line are each transformed with a different expression construct, each expressing a different GPCR and a different barcode to provide, for example, 27 uniquely barcoded cell types. The barcode is based on the use of three surface protein markers exogenous to the cell line and detected at three different fluorescent intensities, using fluorescently labeled antibodies. The different intensities are achieved by having different expression levels of the surface protein markers. Each of the cell types is mixed to form a library. The cells are loaded with a calcium sensitive dye followed by addition of the candidate moiety. After sufficient time for any reaction to have occurred, the cells are then analyzed using flow cytometry detecting four different signals. The signal for the calcium dye indicates that the candidate moiety was an agonist, while the three other signals define the cell type.

Instead of calcium influx, phosphorylated ERK could be used as a marker for GPCR activation. When testing for agonism, the population of barcoded cells would be treated with the sample compound for a certain amount of time, then treated with a fixative and permeabilization reagent to permeabilize the cells and stop all cellular processes. The population would then be stained with an antibody to the phosphorylated form of ERK (1 or 2, or both) as well as the specific signal markers. In this way, activation of a GPCR results in ERK phosphorylation that is identifiable by its unique staining pattern. If the signal needs to be amplified one would overexpress the ERK protein alone or along with other members of the pathway such as MEK. Alternatively, if the GPCR activates the cAMP pathway it will result in the phosphorylation of the CREB protein. This could be detected as described above for phosphorylated ERK.

In a third embodiment, activation of a reporter gene is used to determine the activation of a specific GPCR. In this scenario the population, in addition to the unique identifiers, has a promoter integrated that responds to GPCR activation (such as a calcium responsive promoter, or cAMP responsive promoter, or SRE responsive promoter) that drives the expression of a reporter (detectable agent). The reporter could be a fluorescent protein, enzyme, peptide, proteins, or specific RNA molecule.

In a fourth illustration, if one wishes to determine the effect of a drug on 9 different cell types, typically each of these cell types would have to be grown up individually and screened for their response to the drug. The alternative is to express a combination of markers in each cell type such that the different cell types could be combined in a single sample and the individual cell types could be identified based on their combination of markers. One could use two markers, CD4, and CD8. DNA encoding each of these markers, alone or in combination, could be inserted into each of the 9 populations of cells. Cells that express the marker at levels that allow appropriate discrimination based on detection can then be isolated. That is, one would select cells that express the markers at different levels, which allows for discrimination between the two groups of cells. Table 2 shows how 9 populations could be discriminated by the use of two markers. In this case, the CD4 and CD8 antigens are detected by two different antibodies labeled with different fluorophores, such as FITC and PE.

TABLE 2

|  |  | CD8 expression | | |
| --- | --- | --- | --- | --- |
|  |  | Low | Medium | High |
| CD4 expression | Low | Population 1 | Population 4 | Population 7 |
|  | Medium | Population 2 | Population 5 | Population 8 |
|  | High | Population 3 | Population 6 | Population 9 |

For example, Population 1 is encoded by low expression of both CD4 and CD8. Population 3 also has low CD8 expression, but has high CD4 expression. This allows it to be discriminated from Population 1 by its intensity in the fluorescent channel corresponding to the anti-CD4 antibody. Using three markers, such as CD4, CD8, and CD45R/B220, at low, medium and high levels, one could encode 27 different cell populations. Using four markers, one could encode 81 different cell populations. Of course, by using no marker or zero fluorescence, one has an additional variable. If instead of three populations, four populations are encoded per marker, i.e. unlabeled, low, medium, and high, then combining two markers yields 16 populations, three markers yields 64, and four markers yields 256.

The cell types expressing their specific combination of markers can then each be mixed prior to treatment with the drug. Analysis of the samples is performed on an instrument capable of detecting multiple parameters in single cells, such that both the barcode markers and other analytes of interest, such as DNA levels, ion levels, membrane potential, cell cycle proteins, phospho proteins, and other proteins can be detected simultaneously. These instruments include, but are not limited to, flow cytometers, fluorescent microscopes such as epifluorescent, confocal, spinning disk, and deconvolution, imaging cytometers and other high throughput imaging platforms, as well as mass spectrometers.

The technology can also be applied to library screening. If one wanted to discover genes that were regulated by a specific stimulus, promoter probing using random integration of a reporter-less protein, such as GFP, into the genome is a useful method. Here one would randomly integrate the GFP into the genome and look for cells that increase or decrease the amount of GFP in response to the stimulus. The problem with such an approach is that the random integration of the GFP will result in a wide variety of GFP intensities. Thus when the sample is analyzed as a bulk population, it will be difficult if not impossible to determine whether any of the cells have changed their amount of fluorescence. However if one adds specific markers to the population then the combination of markers would serve to provide a unique identifier to each cell. In the case of library screening many markers will be used. The GFP signal coming from a specific cell or its progeny can then be identified and a determination of the level or change in fluorescence determined.

The technology can also be applied to a plurality of cells that have been modified to express other proteins at the cell surface or intracellularly, that have had certain genes knocked out via siRNA, shRNA, miRNA or other gene modulating mechanisms, that have been modified to allow for detection of gene activation with reporter constructs such as GFP, beta-galactosidase, luciferase; that have been altered to allow for detection of an endpoint assay for screening by luminescence, fluorescence, colorimetric, and other detection methodologies. The technology can be applied to any system in which multiple cell lines are generated and utilized for assays. For example, a cell line such as U937 cells are made to express a specific combination of barcode antigens. The unique identifier antigens could be any of those mentioned above. In this example the unique identifier is an antigen detectable using an antibody (such as CD4, CD8, or B220). The cells are cloned out such that each clone expresses a unique combination of the levels of each antigen (from no expression to high expression). A combination of clones are selected such that a plurality of clones can be combined in a single sample but later identified by their expression levels of the antigens. This library of U937 cells could then be used for any of the aforementioned assay types.

Activation of a reporter gene could also be used to determine the activation of a specific GPCR. In this scenario the population in addition to the unique identifiers, the population has integrated a promoter that responds to GPCR activation (such as a calcium responsive promoter, or cAMP responsive promoter, or SRE responsive promoter) that drives the expression of a reporter (detectable agent). The reporter could be a fluorescent protein, enzyme, peptide, proteins, or specific RNA molecule.

The subject technology also finds application in the case of under or over expression of a protein. Each uniquely labeled cell line is made to overexpress a specific protein (or library of mutant proteins), peptide, RNA molecule, or other biological molecule. The population of cells overexpressing the molecules is then assayed for the effects of overexpression of that molecule on cellular functions and signaling. By identifying the specific markers on the cells, one determines which molecule was responsible for the specific effect. For example, one can overexpress proteins believed to play a role in a particular signaling pathway. These cells can then be assayed for phosphorylation levels of a downstream member of the signaling cascade. Cell lines overexpressing upstream members of the cascade are identified via an increase of phosphorylation measured in the downstream member.

In the opposite approach, specific genes could be targeted by siRNA constructs, or other gene-knockdown methodologies, that reduce the expression of a target gene. Genes could also be eliminated through homologous recombination methods. This would create libraries of cells that are lacking or have reduced protein levels of a specific protein or group of proteins in uniquely identifiable cells. The mixed population could then be assayed for the effects of these manipulations on cellular functions, such as response to stimulus or altered growth patterns. Since each cell line can be uniquely identified and has been manipulated in a specific manner it would be possible to determine what manipulation led to the observable change in response. For example, in studying a particular signaling cascade, one can measure the increase in phosphorylation of a downstream member of the cascade in response to an extracellular stimulus. This can be measured in control cells, and in those that have been altered to reduce expression of particular proteins by siRNA or other method. In cell lines MB-453, HBL100, MDAMB134, MDAMB175, MDA-MB-330, MDA-MB-361, MDA-MB-415, MDA-MB-469, SK-BR-5, SK-BR-7, and ZR75-30.

In the first step in generating the barcoded cell lines, expression vectors for the marker proteins are prepared. The murine forms of CD4, CD8, and CD45R/B220 are employed. Because the antigens are murine and the cell lines being used are human, background is further reduced as endogenous proteins will not be recognized by the antibodies. The truncated forms of these surface proteins are PCR amplified from cDNA derived from murine splenocytes. The proteins are truncated to eliminate intracellular portions to prevent any effect of overexpressing these proteins on cellular signaling. The PCR amplified products are subcloned into an MFG-based Moloney Murine Leukemia viral vector and sequenced to ensure their integrity. The use of a retroviral system to insert the surface markers into the cell lines is advantageous due to higher transduction efficiency and more stable expression than typical transfection methods.

In order to barcode the 27 breast cancer cell lines, virus is produced from the CD4, CD8, and B220 viral expression vectors and pooled. The pooled virus is then used to infect each of the 27 cell lines. The cell lines are then analyzed by flow cytometry for expression of the surface markers. For those cells for which the infection efficiency is not high enough to get triply infected cells, positive cells are sorted by FACS and re-infected with the appropriate virus. Once triply infected cells are available for the 27 cell lines, each cell line is clonally sorted for a pre-selected expression level of the three markers. Three intensities (up to six could be used) are chosen for each of the three surface markers; no detectable expression, low, and high. This provides 27 possible combinations exactly matching the number of cell lines to be labeled (see Table 3 for the subject barcoding signature scheme). Once the clones have grown out of the 96-well dish they are analyzed by flow cytometry. Those clones showing the appropriate levels of each of the three markers with the smallest coefficients of variation are then expanded and frozen.

TABLE 3

CD4, CD8, and B220 barcode matrix to encode 27 different cell lines.

| | | Cell Line Number | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| Barcode | CD4 | − | − | − | − | − | − | − | − | − | + | + | + | + | + | + | + | + | + | ++ | ++ | ++ | ++ | ++ | ++ | ++ | ++ | ++ |
| Antigen | CD8 | − | − | − | + | + | + | ++ | ++ | ++ | − | − | − | + | + | + | ++ | ++ | ++ | − | − | − | + | + | + | ++ | ++ | ++ |
| Levels | B220 | − | + | ++ | − | + | ++ | − | + | ++ | − | + | ++ | − | + | ++ | − | + | ++ | − | + | ++ | − | + | ++ | − | + | ++ |

− = no expression
+ = low expression
++ = high expression where a critical member of the signaling pathway has been removed, one expects to find reduced phosphorylation. Using the barcode signature, one could rapidly identify which cell line, and therefore which gene, is responsible for this decrease.

The following is a more detailed description of the application of the subject invention. A panel of barcoded human breast cancer cell lines is generated. The 27 cell lines to be barcoded are selected to encompass the NCI, MD Anderson, and Ludwig Cancer institute studies. These are: MDA-MB-468, BT-549, T-47D, MDA-MB-435, HS 578T, MDA-MB-231, MCF7, BT-20, BT-474, MDA-MB-361, SK-BR-3, ZR-75-1, DU4475, MDA-MB-157, MDA-MB-436, MDA- With this library, a number of assays can be performed:

1) Cell cycle analysis using DAPI (4',6-diamidino-2-phenylindole): Cell cycle analysis using DAPI is a standard method of determining cell cycle [20].

2) Cell proliferation: Since the 27 cell lines are run as a mixture the relative numbers of each of the cell lines will always be known. However, if a compound reduces the numbers of all of the cell lines then this ratio would stay the same and not be indicative of an effect on cell proliferation. The absolute number of cells will be determined by including a fixed amount of fluorescently labeled polystyrene beads (such as TruCount beads from Becton Dickinson) in the solution prior to flow cytometric analysis. These beads provide a reference that is used to calculate the number of cells per sample volume. Critically, the beads are of a uniform and distinct size relative to the cell lines, and can therefore be easily identified by forward and side scatter characteristics on the cytometer. From this number, the absolute number of each cell line will be determined and compared to untreated controls.

3) Apoptosis: In order to determine the number of apoptotic cells in the culture, one uses an antibody specific to the activated form of Caspase-3. Caspase-3 is synthesized in an inactive form that is cleaved during the early stages of apoptosis. The cleaved form is detected using the antibody and can be used as a measure of the number of apoptotic cells in a fixed sample.

4) Detection of DNA damage: p53 is phosphorylated in response to DNA damage at several residues. Serine 15 is phosphorylated by ATM, ATR, and DNA-PK and is critical to p53 interaction with MDM2, its negative regulator. Therefore, to detect DNA damage in our cell population an antibody specific against p53 phosphorylated at Ser15 (available from Cell Signaling Technology) is conjugated to Alexa 488 or Alexa 647 (two small molecule dyes with simple conjugation and purification methodologies). The cell pool is treated with stimulus then fixed, permeabilized, and stained with antibodies to the barcode antigens as well as the phospho-specific p53 Ser15 antibody.

In order to combine the assays it is imperative to assess the function of each antibody conjugated to multiple fluorophores. Certain fluorophores are more readily detected on the flow cytometer, and therefore lend themselves to larger/more robust assay windows. By matching the least robust assays with the most robust fluorophores one is able to manage the simultaneous assessment of these experimental parameters.

5) Cell Stress: p38 is a stress activated protein kinase (SAPK) that is activated in response to cellular stresses such as osmotic shock, temperature fluctuation, neutrient deprivation, UV exposure, and other metabolic imbalances. Therefore, its activity and phosphorylation can be used as a surrogate for cellular stress.

TABLE 4

Staining panel to analyze 27 cell lines simultaneously for 5 assay parameters

| Parameter | Antibody/Reagent | Fluorophore |
|---|---|---|
| Barcode Antigens | | |
| CD4 | Anti-CD4 mAb | PE-Cy7 |
| CD8 | Anti-CD8 mAb | PE-Cy5.5 |
| B220 | Anti-B220 mAb | APC-Cy7 |
| Cell Cycle | DAPI | DAPI (Pacific Blue detector) |
| Cell Number | Polystyrene Beads | Unique scatter and fluorescence relative to cell lines |
| Apoptosis | Anti-Cleaved Caspase-3 mAb | PE |
| DNA Damage | Anti-p53 (pS15) mAb | Alexa 488 |
| Cellular Stress | Anti-p38 (pT180/pY182) mAb | Alexa 647 |

The subject method allows for the convenience of having kits comprising a library of cells sharing a characteristic of interest. In addition to the cells, labeled reagents for detection of the barcode can be included, such as labeled antibodies. Also included may be reagents for the specific assay of interest, such as calcium sensitive dyes, DNA dyes, vital dyes, phospho-specific antibodies, antibodies to specific cellular proteins, etc.

It is evident from the above results that the subject technology greatly broadens the ability to perform a variety of operations with a mixture of cells and then determine on an individual cell basis the effect of the operation. Such capability finds broad application in a variety of arenas.

The following examples are offered by way of illustration and not by way of limitation.

EXPERIMENTAL

Genetic Barcoding

Figure 1:
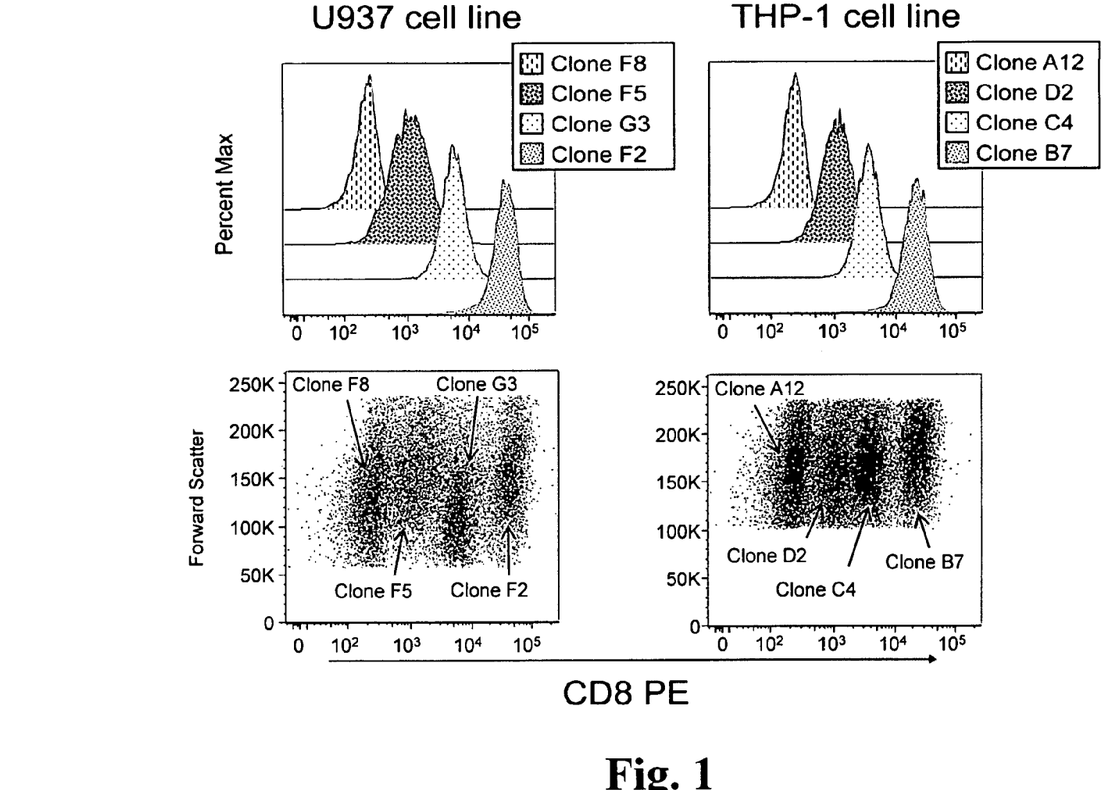
FIG. 1. Genetic barcoding of four populations of cells using one genetic marker, CD8, displayed on the cell surface. Each population of cells expresses a different level of CD8 on the surface. For both U937 and THP-1 cells four populations in a single channel (PE) can be identified. These cells were clonally isolated by limiting dilution.
Figure 2:
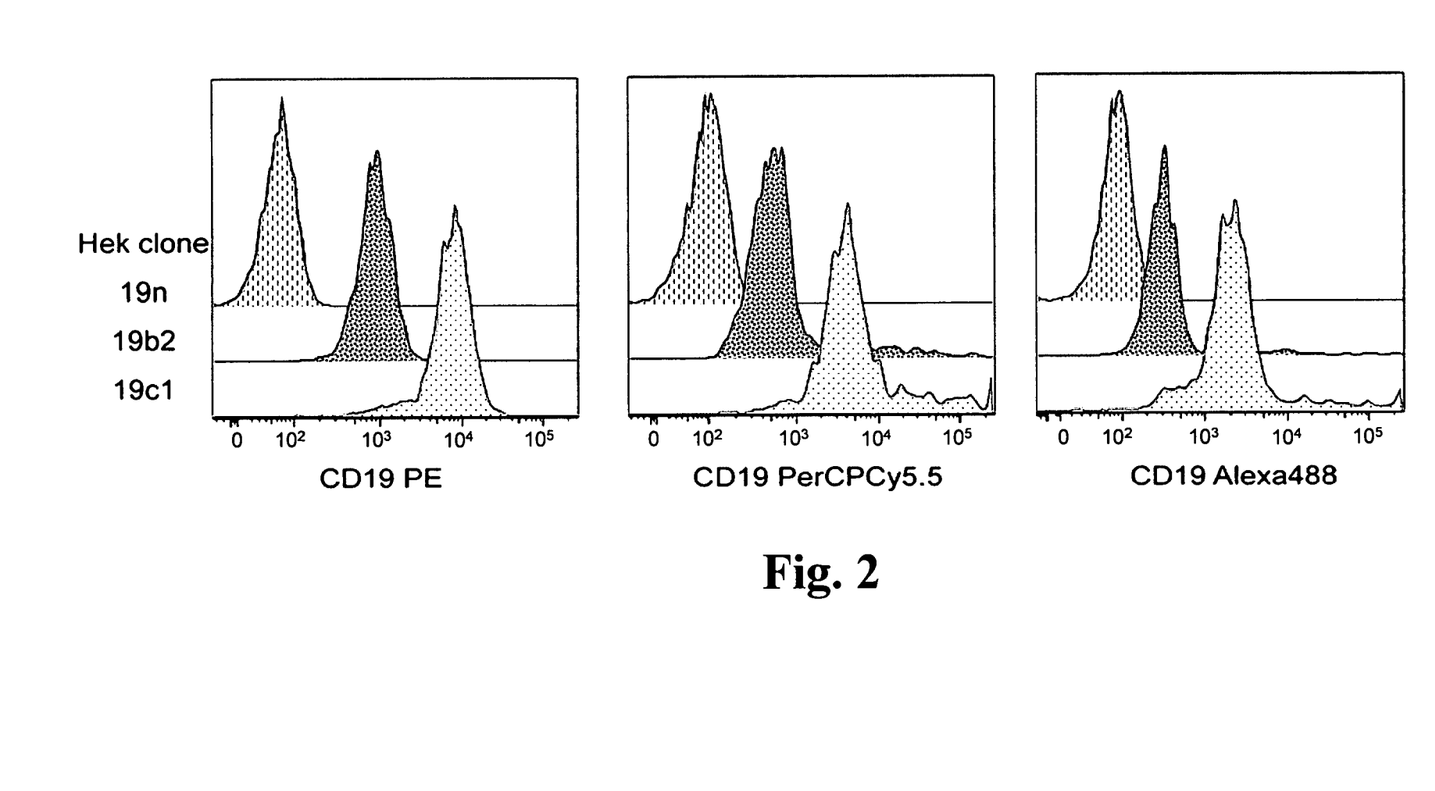
FIG. 2. Staining of genetically barcoded cell populations with antibodies conjugated to three different fluorescent molecules. Human Hek293 cells were transduced with a vector containing murine CD19, and three clones were sorted by FACS based on their expression level of the signal marker. Shown in this figure is staining of three clones with three different fluorescently-labeled anti-CD19 antibodies. The fluorophores used were phycoerythrin (PE), PerCPCy5.5, and Alexa Fluor 488. Note that the three populations are distinguished in all three fluorescent parameters.
Figure 3:
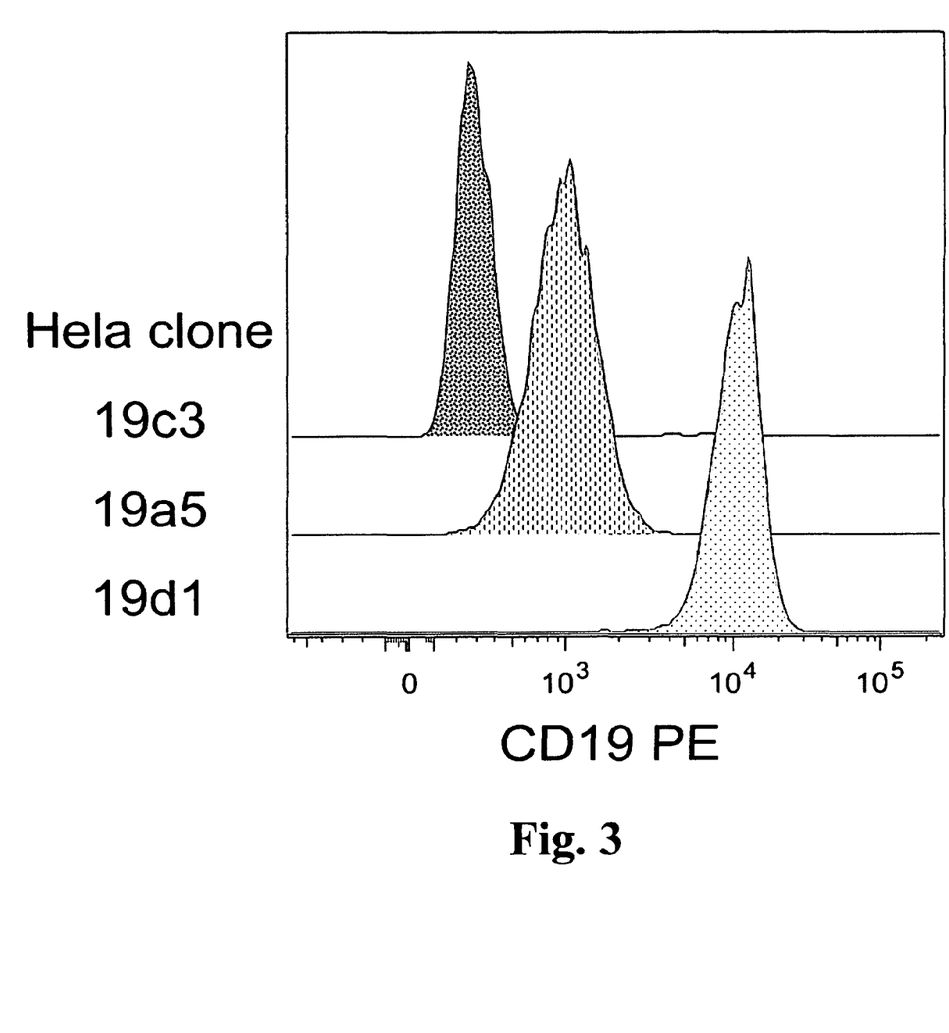
FIG. 3. Barcoding of Hela cells at three levels with CD19. Human Hela cells were transduced with a virus containing murine CD19 and three clones were sorted by FACS based on their expression level of the signal marker CD19. Shown in this figure is analysis of the clones after expansion. Cells were trypsinized from the culture dish, washed with staining medium, then stained with anti-CD19 antibody conjugated to PE.
Figure 4A:
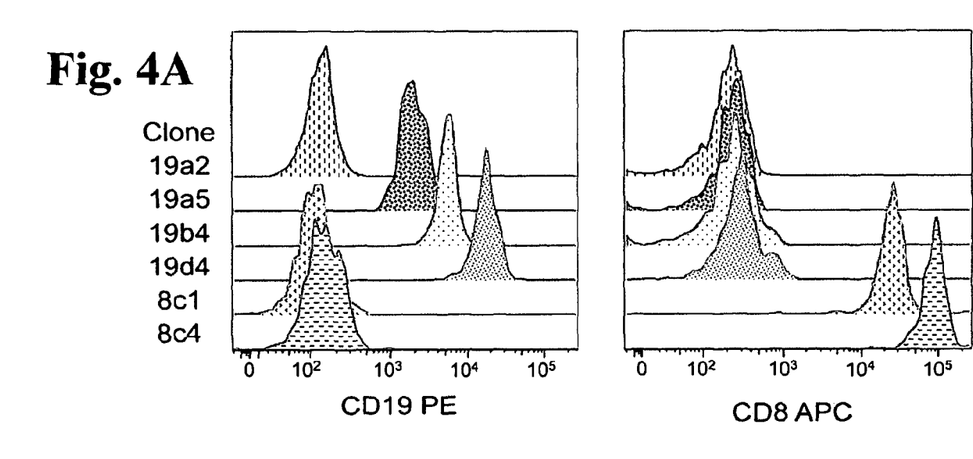
Figure 4B:
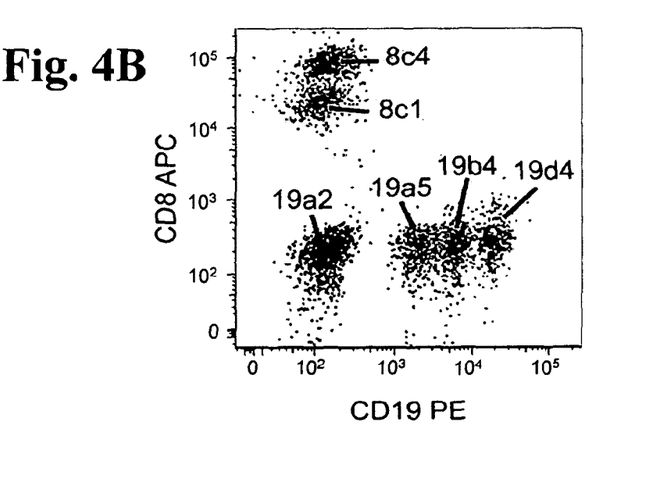
Figure 5A:
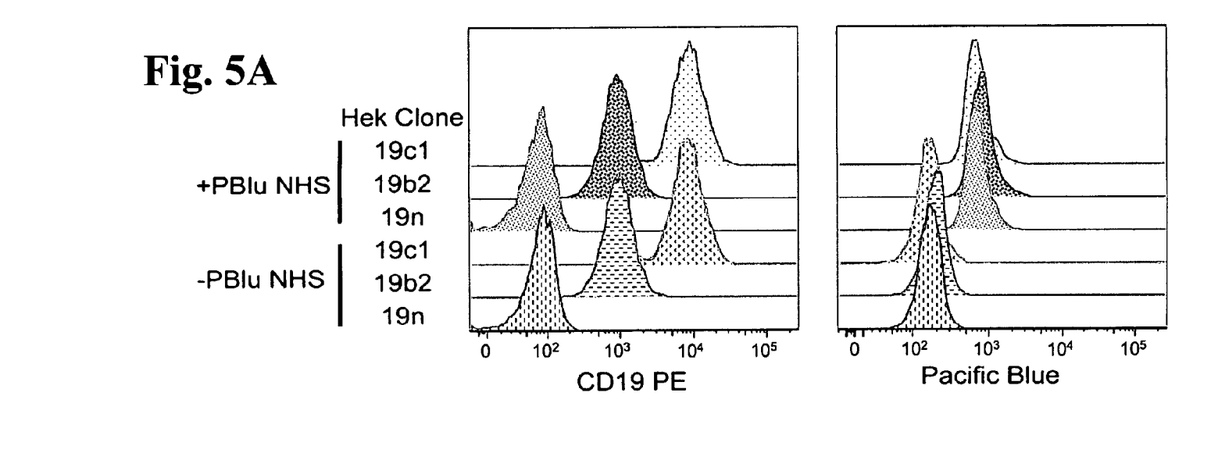
Figure 5B:
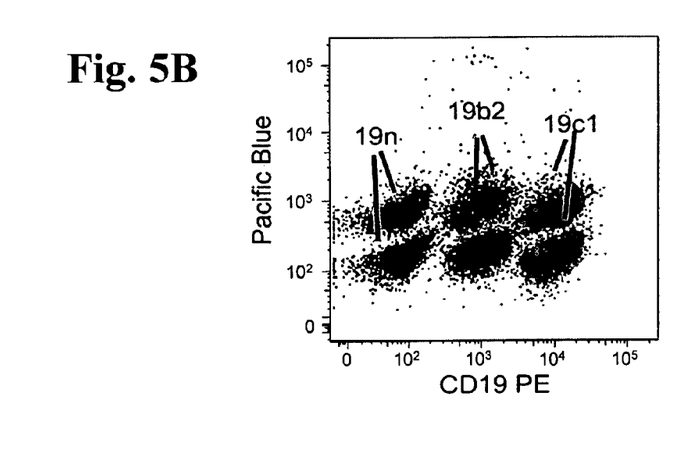
Figure 6:
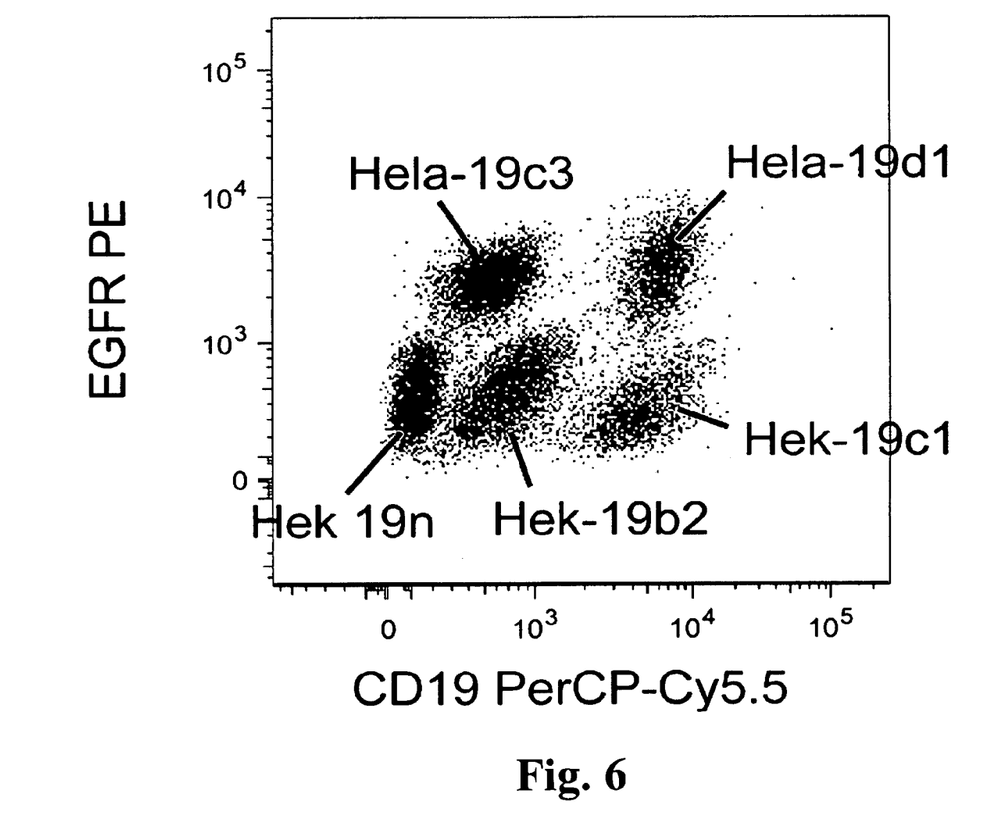

In this example U937 and THP-1 cells (human monocyte cell lines) were transduced with a retroviral vector encoding murine CD8 (CD8). Single cells were placed into each well of a 96-well dish in the appropriate growth medium (RPMI+ 10% FBS+Penicillin-Streptomycin and glutamine). Once the clones had grown to a sufficient density, they were placed on ice and stained with an anti-CD8 antibody that was previously conjugated to Phycoerythrin (PE) according to standard procedures. The cells were then analyzed by flow cytometry for their level of expression of CD8. Four clones expressing the desired amount of CD8 are shown that express sufficiently different amounts of CD8 such that they can be uniquely identified.

Although the invention has been described with reference to the above examples, it will be understood that modifications and variations are encompassed within the spirit and scope of the invention. Accordingly, the invention is limited only by the following claims. All references referred to in the specification are incorporated by reference as if fully set forth therein.

1. Russello, S. V. (2004). Assessing cellular protein phosphorylation: high throughput drug discovery technologies. Assay Drug Dev Technol 2, 225-235.
2. Hood, L., and Perlmutter, R. M. (2004). The impact of systems approaches on biological problems in drug discovery. Nat Biotechnol 22, 1215-1217.
3. Chapman, T. (2004). Drug discovery: the leading edge. Nature 430, 109-115.
4. Suggitt, M., and Bibby, M. C. (2005). 50 years of preclinical anticancer drug screening: empirical to target-driven approaches. Clin Cancer Res 11, 971-981.
5. Tarnok, A., Bocsi, J., and Brockhoff, G. (2006). Cytomics—importance of multimodal analysis of cell function and proliferation in oncology. Cell Prolif 39, 495-505.
6. Krutzik, P. O., Clutter, M. R., and Nolan, G. P. (2005). Coordinate analysis of murine immune cell surface markers and intracellular phosphoproteins by flow cytometry. J Immunol 175, 2357-2365.
7. Krutzik, P. O., Crane, J. M., Clutter, M. R., and Nolan, G. P. (2008). High-content single-cell drug screening with phosphospecific flow cytometry. Nat Chem Biol 4, 132-142.
8. Krutzik, P. O., Hale, M. B., and Nolan, G. P. (2005). Characterization of the murine immunological signaling network with phosphospecific flow cytometry. J Immunol 175, 2366-2373.
9. Krutzik, P. O., Irish, J. M., Nolan, G. P., and Perez, O. D. (2004). Analysis of protein phosphorylation and cellular signaling events by flow cytometry: techniques and clinical applications. Clin Immunol 110, 206-221.
10. Krutzik, P. O., and Nolan, G. P. (2003). Intracellular phospho-protein staining techniques for flow cytometry: monitoring single cell signaling events. Cytometry A 55, 61-70.

11. Krutzik, P. O., and Nolan, G. P. (2006). Fluorescent cell barcoding in flow cytometry allows high-throughput drug screening and signaling profiling. Nat Methods 3, 361-368.

12. Sklar, L. A., Carter, M. B., and Edwards, B. S. (2007). Flow cytometry for drug discovery, receptor pharmacology and high-throughput screening. Curr Opin Pharmacol.

13. Zhu, Y., Wang, A., Liu, M. C., Zwart, A., Lee, R. Y., Gallagher, A., Wang, Y., Miller, W. R., Dixon, J. M., and Clarke, R. (2006). Estrogen receptor alpha positive breast tumors and breast cancer cell lines share similarities in their transcriptome data structures. Int J Oncol 29, 1581-1589.

14. Shoemaker, R. H. (2006). The NCI60 human tumour cell line anticancer drug screen. Nat Rev Cancer 6, 813-823.

15. Harris, R. A., Yang, A., Stein, R. C., Lucy, K., Brusten, L., Herath, A., Parekh, R., Waterfield, M. D., O'Hare, M. J., Neville, M. A., Page, M. J., and Zvelebil, M. J. (2002). Cluster analysis of an extensive human breast cancer cell line protein expression map database. Proteomics 2, 212-223.

16. Williams, K., Chubb, C., Huberman, E., and Giometti, C. S. (1998). Analysis of differential protein expression in normal and neoplastic human breast epithelial cell lines. Electrophoresis 19, 333-343.

17. Holbeck, S. L. (2004). Update on NCI in vitro drug screen utilities. Eur J Cancer 40, 785-793.

18. Feng, X. D., Huang, S. G., Shou, J. Y., Liao, B. R., Yingling, J. M., Ye, X., Lin, X., Gelbert, L. M., Su, E. W., Onyia, J. E., and Li, S. Y. (2007). Analysis of Pathway Activity in Primary Tumors and NCI60 Cell Lines Using Gene Expression Profiling Data. Genomics Proteomics Bioinformatics 5, 15-24.

19. Paull, K. D., Shoemaker, R. H., Hodes, L., Monks, A., Scudiero, D. A., Rubinstein, L., Plowman, J., and Boyd, M. R. (1989). Display and analysis of patterns of differential activity of drugs against human tumor cell lines: development of mean graph and COMPARE algorithm. J Natl Cancer Inst 81, 1088-1092.

20. Tan, T. W., Tsai, H. R., Lu, H. F., Lin, H. L., Tsou, M. F., Lin, Y. T., Tsai, H. Y., Chen, Y. F., and Chung, J. G. (2006). Curcumin-induced cell cycle arrest and apoptosis in human acute promyelocytic leukemia HL-60 cells via MMP changes and caspase-3 activation. Anticancer Res 26, 4361-4371.

What is claimed is:

1. A method of distinguishing between cell types in a sample comprising a plurality of different cell types comprising:
    a) labeling at least two different signal markers expressed by at least one cell type in the sample with distinguishably labeled binding proteins, wherein the at least two different signal markers are exogenous cell surface proteins, wherein said exogenous cell surface proteins are constitutively expressed from one or more genetic constructs, and wherein at least one of said signal markers is expressed at least at three different amounts in said plurality of different cell types;
    b) detecting from at least one cell type of said plurality of different cell types the at least two different, distinguishably labeled signal markers;
    c) measuring at least one of said labeled signal markers of step b) at three different intensities corresponding to said at least three different amounts in the plurality of different cell types, wherein the combination of the intensity and type of signal markers in a single cell type provides a unique barcode; and
    d) distinguishing at least one cell type of said plurality of different cell types based on the unique barcode provided in c).

2. The method of claim 1, wherein said labeled binding protein is selected from the group consisting of an antibody, an enzyme and a lectin.

3. The method of claim 2, wherein said labeled binding protein comprises a label selected from the group consisting of a fluorescer, an isotope, a metal atom, an ion and a chemiluminescer.

4. The method of claim 1, wherein detecting is by fluorescence and said three different intensities are measured as absence of fluorescence, fluorescence at one intensity and fluorescence at a second different intensity.

5. The method of claim 4, wherein at least two different cell types are labeled to fluoresce at different wavelengths.

6. The method of claim 1, wherein said labeled binding proteins comprise antibodies with different binding affinities.

7. The method of claim 6, wherein the antibodies with different binding affinities are distinguishably labeled.

8. The method of claim 1, wherein the cell type comprising the genetic construct is a transformed cell line.

9. The method of claim 1, wherein said plurality of different cell types further comprises an identifiable response marker distinguishable from said signal markers, wherein said signal markers and said identifiable response marker are distinguishably labeled.

10. The method of claim 9, wherein said identifiable response marker is a labeled intracellular protein.

11. The method of claim 10, wherein said intracellular protein is fluorescently labeled.

12. The method of claim 9, wherein said identifiable response marker exhibits a change corresponding to an effect on a cellular pathway.

13. The method of claim 12, wherein the change in the identifiable response marker is selected from the group consisting of degradation, phosphorylation, acylation, acetylation, sumoylation, ubiquitination, complex formation, initiation of transcription, inhibition of transcription, initiation of expression, inhibition of expression, enzyme activation, enzyme inhibition, receptor dimerization, receptor complexing, receptor binding, receptor activation and receptor internalization.

14. The method of claim 1, wherein said labeling comprises combining said plurality of different cell types with antibodies to said signal markers prior to detecting, wherein said antibodies are conjugated to at least one detectable moiety.

15. The method of claim 14, wherein said detectable moiety is selected from different fluorescers, different numbers of fluorescers, and mass isotope labels.

16. The method of claim 15, wherein said detectable moiety is a fluorescer and said detecting is by flow cytometry.

17. The method of claim 15, wherein said detectable moiety is a mass isotope label and said detecting is by mass spectrometry.

18. The method of claim 1, wherein said plurality of cell types comprises at least 6 different cell types.

19. The method of claim 1, further comprising fixing and permeabilizing said plurality of different cell types.

20. A method of distinguishing between cell types in a sample comprising at least 6 different cell types comprising:
    a) labeling at least two different signal markers expressed by at least one cell type in the sample with fluorescently labeled antibodies, wherein the at least two different signal markers are exogenous cell surface proteins, wherein said at least two signal markers are distinguishably labeled, and wherein said exogenous cell surface proteins are constitutively expressed from one or more genetic constructs;

b) detecting from at least one cell type of said 6 different cell types the at least two different, distinguishably labeled signal markers by flow cytometry, wherein at least one of said signal markers is expressed at least at three different amounts in said at least 6 different cell types;

c) measuring at least one of said labeled signal markers of step b) at three different intensities, wherein the combination of the intensity and type of signal markers in a single cell type provides a unique barcode; and d) distinguishing at least one cell type of said plurality of different cell types based on the unique barcode provided in c).

21. The method of claim 20, wherein said antibodies are specific for said cell surface proteins.

22. The method of claim 20, wherein said antibodies are conjugated to different fluorescers or different numbers of fluorescers.

23. A mixture of cells comprising at least 6 different cell types, wherein:

a) each cell type comprises at least two genetic constructs which express cell surface proteins exogenous to said cell types;

b) at least on of said cell surface proteins is configured to be expressed at least at three different amounts with a different amount in each of said cell types, wherein the expression of the at least one cell surface protein is detectable at least at three different intensities; and c) said cell types can be distinguished by detecting binding of labeled antibodies to each of said cell surface proteins of each cell, wherein each cell surface protein binds to a distinguishably labeled antibody.

24. The mixture of 23, wherein said labeled antibodies are bound to each of said cell surface proteins.

* * * * *